US008653826B2

(12) United States Patent
Liu et al.

(10) Patent No.: US 8,653,826 B2
(45) Date of Patent: Feb. 18, 2014

(54) CONNECTOR MONITORING ASSEMBLY AND A DETECTOR ASSEMBLY INCLUDING THE SAME

(75) Inventors: James Zhengshe Liu, Glenview, IL (US); Donald Langler, Brookfield, WI (US); Scott Petrick, Sussex, WI (US)

(73) Assignee: General Electric Company, Schenectady, NY (US)

( * ) Notice: Subject to any disclaimer, the term of this patent is extended or adjusted under 35 U.S.C. 154(b) by 753 days.

(21) Appl. No.: 12/763,012

(22) Filed: Apr. 19, 2010

(65) Prior Publication Data
US 2011/0254563 A1    Oct. 20, 2011

(51) Int. Cl.
*G01R 31/04*    (2006.01)
(52) U.S. Cl.
CPC .................................. *G01R 31/045* (2013.01)
USPC ......................................................... 324/538
(58) Field of Classification Search
None
See application file for complete search history.

(56) References Cited

U.S. PATENT DOCUMENTS

| | | | |
|---|---|---|---|
| 4,232,262 A * | 11/1980 | Emo et al. | 324/722 |
| 5,491,424 A * | 2/1996 | Asar et al. | 324/715 |
| 6,999,121 B2 | 2/2006 | Endo | |
| 7,342,998 B2 | 3/2008 | Kump et al. | |
| 7,429,737 B2 | 9/2008 | Wojcik et al. | |
| 7,488,946 B2 | 2/2009 | Hennessy et al. | |
| 7,541,591 B2 | 6/2009 | Endo et al. | |
| 2007/0140424 A1 | 6/2007 | Serceki | |
| 2008/0240358 A1 | 10/2008 | Utschig et al. | |
| 2009/0129547 A1 | 5/2009 | Jabri et al. | |

\* cited by examiner

*Primary Examiner* — Paresh Patel
(74) *Attorney, Agent, or Firm* — The Small Patent Law Group; Dean D. Small

(57) ABSTRACT

A method of monitoring the voltage transmitted through a pair of electrical connector devices is provided. The pair of electrical connector devices include a source connector coupled to a power supply and a load connector coupled to a load, the source connector being coupled to the load connector. The method includes determining the voltage utilized by the load, determining the voltage generated by the power supply, and determining an electrical resistance of the pair of electrical connectors using the determined voltage utilized by the load and the voltage generated by the power supply. A connector monitoring circuit and a portable X-ray detector including the connector monitoring circuit is also provided.

21 Claims, 9 Drawing Sheets

CONNECTOR MONITORING ASSEMBLY AND A DETECTOR ASSEMBLY INCLUDING THE SAME

BACKGROUND OF THE INVENTION

The subject matter disclosed herein relates generally to imaging detectors, and more particularly to a device for monitoring a docking connector on a portable imaging detector.

In various medical imaging applications, a portable detector may be utilized to perform medical imaging. During operation, X-rays pass through an object being imaged and impinge on a plurality of detector elements of the portable detector. The detector elements produce an electrical signal that represents the intensity of the impinging X-ray beam and hence allows estimation of the attenuation of the beam as the beam passes through the object.

Portable detectors may be used in both mobile and fixed applications. For example, when the portable detector is operated in a mobile application, a battery housed within the portable detector may be used to power the portable detector. Optionally, the portable detector may be coupled to a remote imaging system via a tether that is coupled to a connector, often referred to as a docking connector, that is located on the housing of the portable detector. The portable detector then receives power from and communicates with the remote workstation via the tether. In a fixed application, the portable detector is inserted into a docking station. The docking station includes a connector that couples directly to the connector on the portable detector. The portable detector then receives power from and communicates with the remote workstation via the docking station.

Over the operational lifetime of the portable detector, the portable detector is coupled and uncoupled from either the tether or the docking station many times, often referred to as mating cycles. Each mating cycle results in wear to the docking connector. Moreover, each mating cycle may cause the docking connector to be contaminated with dust, chemicals, and/or patient body fluids. As a result, the docking connector may have to be cleaned and/or replaced.

However, it is difficult for the operator to determine whether the docking connector has failed and therefore should be replaced or whether the docking connector merely requires cleaning. As a result, a service technician must perform numerous tests on the docking connector to determine whether the docking connector requires cleaning or replacement.

BRIEF DESCRIPTION OF THE INVENTION

In one embodiment, a method of monitoring the voltage transmitted through a pair of electrical connector devices is provided. The pair of electrical connector devices include a source connector coupled to a power supply and a load connector coupled to a load, the source connector being coupled to the load connector. The method includes determining the voltage detected at the load, determining the voltage generated by the power supply, and determining an electrical resistance of the pair of electrical connectors using the determined voltage utilized by the load and the voltage generated by the power supply.

In another embodiment, a connector monitoring assembly is provided. The connector monitoring assembly includes an analog-to-digital converter, and a processor coupled to the analog-to-digital converter. The processor is programmed to determine a voltage detected by a load, determine a voltage generated by a power supply, and determine an electrical resistance of a pair of electrical connectors using the determined voltage utilized by the load and the voltage generated by the power supply, the pair of electrical connector devices including a source connector coupled to the power supply and a load connector coupled to the load, the source connector being coupled to the load connector.

In a further embodiment, a portable X-ray detector is provided. The portable X-ray detector includes a detector panel including a plurality of detector elements, a docking connector configured to provide electrical power to the detector panel, the docking connector configured to couple to a power connector, and a connector monitoring assembly coupled to the docking connector. The connector monitoring assembly configured to determine a voltage detected by a detector panel, determine a voltage generated by a power supply, and determine an electrical resistance of the docking connector using the determined voltage utilized by the detector panel and the voltage generated by the power supply.

DETAILED DESCRIPTION OF THE INVENTION

Figure 1:
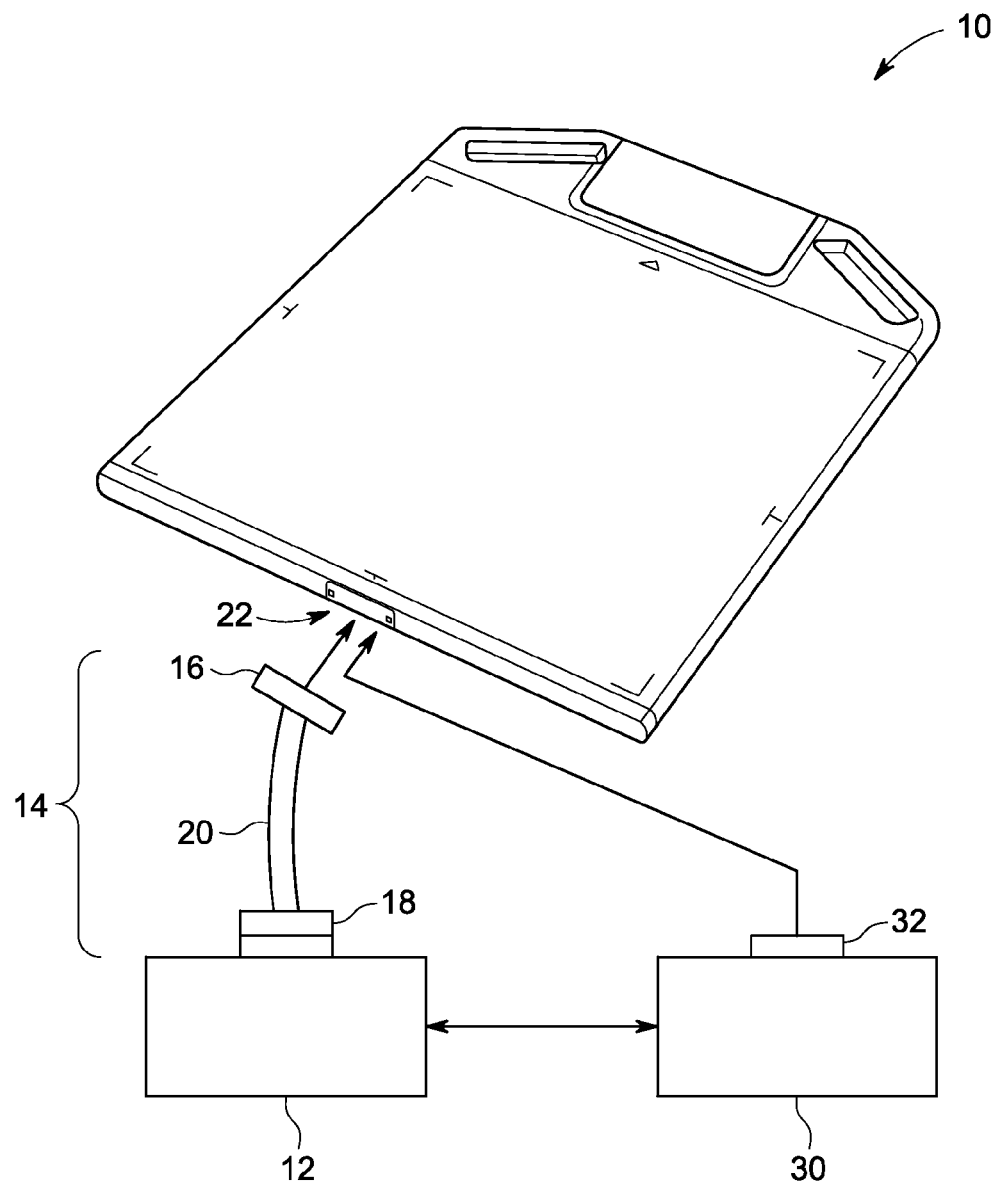
FIG. 1 is a pictorial view of an exemplary portable medical imaging detector coupled to a medical imaging system in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

FIG. 1 is a pictorial view of a portable medical imaging detector 10 configured to be coupled to an exemplary medical imaging system 12. In the exemplary embodiment, the portable detector 10 is configured to be hand-carried by an operator to various locations to perform, for example, medical imaging. Additionally, the portable detector 10 may be mounted on a wheeled cart or other movable apparatus to enable an operator to move the detector 10 from one location to another location. In one mode of operation, when the portable detector 10 is operated in a mobile application, a battery (not shown) housed within the portable detector 10, may be used to power the portable detector 10. Optionally, the portable detector 10 may receive power from, and communicate with, a remote medical imaging system 12, via a tether 14. The tether 14 includes a first connector 16, referred to herein as the source connector 16, a second connector 18, and an electrical lead 20 coupled between the first and second connectors 16 and 18. During operation, the source connector 16 is configured to couple to, or mate with, a connector 22, referred to herein as a load or docking connector 22. The second connector 18 is configured to couple to the medical imaging system 12. The combination of the source connector 16 and the load connector 22 is referred to herein as a mating pair or a pair of electrical connectors. When the source connector 16 is coupled to the load connector 22, the remote medical imaging system 12 transmits power to, and receives information from, the portable detector 10 via the tether 14.

In the fixed application, the portable detector 10 is inserted into a docking station 30. The docking station 30 includes a connector 32 that is configured to couple to or mate directly with the docking connector 22 on the portable detector 10. During operation, the portable detector 10 receives power from, and communicates with, the remote medical imaging system 12 via the docking station 30. The combination of the docking connector 22 and the connector 32 is also represents a mating pair or a pair of electrical connectors. Connectors 16 and 32 may be repeatedly coupled and uncoupled to a docking connector 22 shown in FIG. 1.

Figure 2:
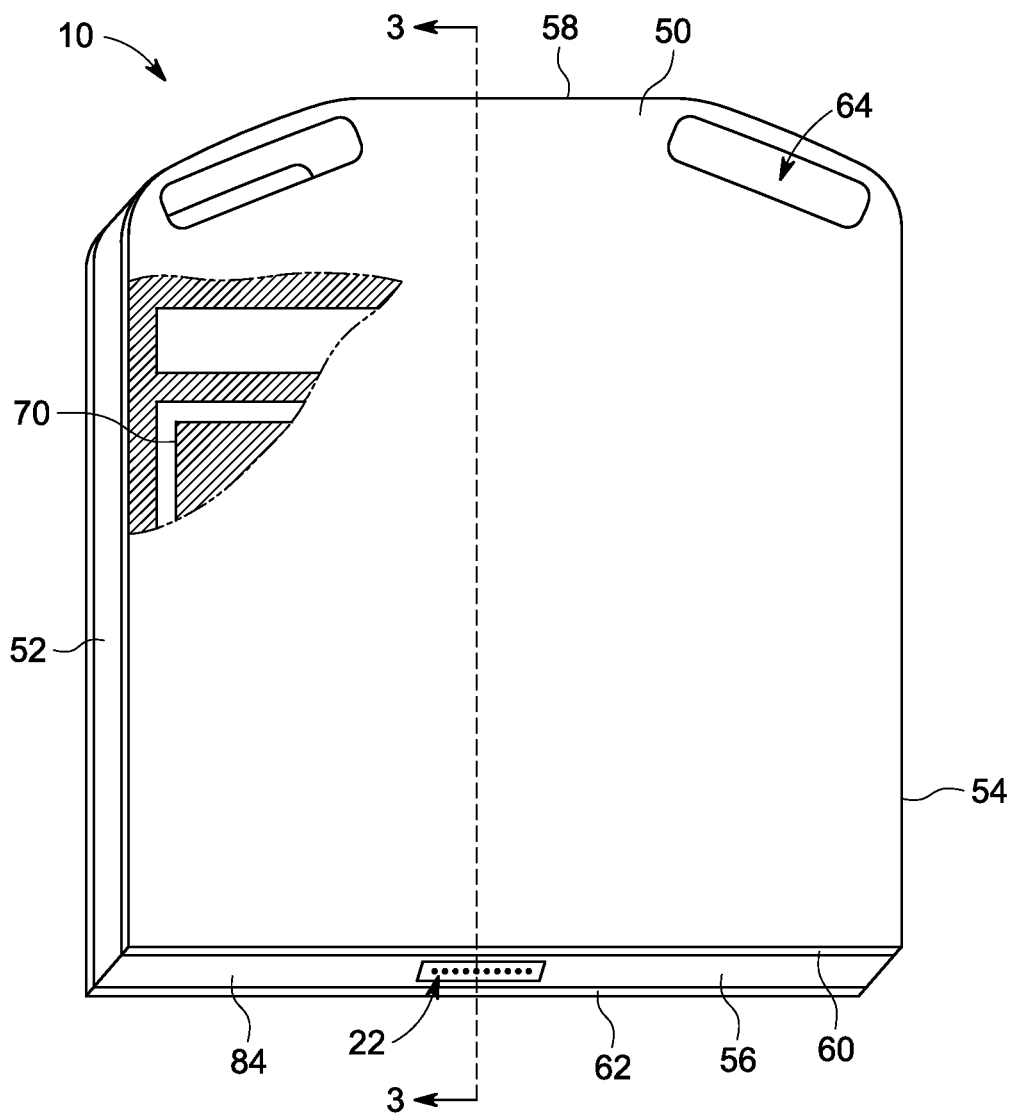
FIG. 2 is a top cut-away view of the exemplary portable detector shown in FIG. 1 in accordance with an embodiment of the present invention.

FIG. 2 is a top cut-away view of the portable detector 10 shown in FIG. 1. During operation, a connector monitoring assembly, discussed in more detail below, is configured to enable an operator to determine when the docking connector 22 should be cleaned or replaced. Although the operation of the connector monitoring circuit is explained with reference to the docking connector 22, it should be realized that the connector monitoring circuit may also be used to determine when at least one of the connector 16 and/or the connector 32 should be cleaned or replaced. In the exemplary embodiment, the connector monitoring circuit utilizes various measurements to determine the electrical conductivity of the mating pair, e.g. connector 16 mating with the docking connector 22.

The electrical conductivity of the mating pair is then utilized to determine the wear on the docking connector 22 and also determine whether the docking connector 22 should be cleaned or replaced. Electrical conductivity, as used herein, refers to the ability of the mating pair to conduct electricity. Accordingly, as wear on the mating pins of the docking connector 22 increases, the surface area of the mating pins decreases such that the docking connector 22 may not be firmly or securely coupled to the connector 16. A disturbance, such as wear or contamination, of the electrical connection between the docking connector 22 and the connector 16 may also result in a decrease of the electrical conductivity through the mating pair. The decrease in electrical conductivity is generally proportional to an increase in the resistivity of the mating pair. As such, the connector monitoring circuit is configured to determine when at least one of the docking connector 22 or the connector 16 should be cleaned or replaced based on the measured resistivity of the mating pair.

As shown in FIG. 2, the portable detector 10 includes a casing 50. The casing 50 is formed to include a pair of sidewalls 52 and 54, a bottom side 56, and an opposing top side 58. The casing 50 also includes a front cover 60, shown as a surface parallel to the plane of the illustration, and an opposing back cover 62. The casing also includes a handle 64 that extends from the front cover 60 to the back cover 62. During operation, the handle 64 enables an operator to transport the portable detector 10. Specifically, the handle 64 can be used to facilitate mounting, carrying and/or storing the portable detector 10. The sidewalls, top and bottom walls, the front and back covers together form the casing 50. The casing 50 may be made of a lightweight, low atomic number (N) material, such as aluminum, or a graphite material. Graphite has a lower weight than aluminum, but it is also stiffer and less energy-absorbent. As discussed above, the portable detector 10 also includes the docking connector 22.

Figure 3:
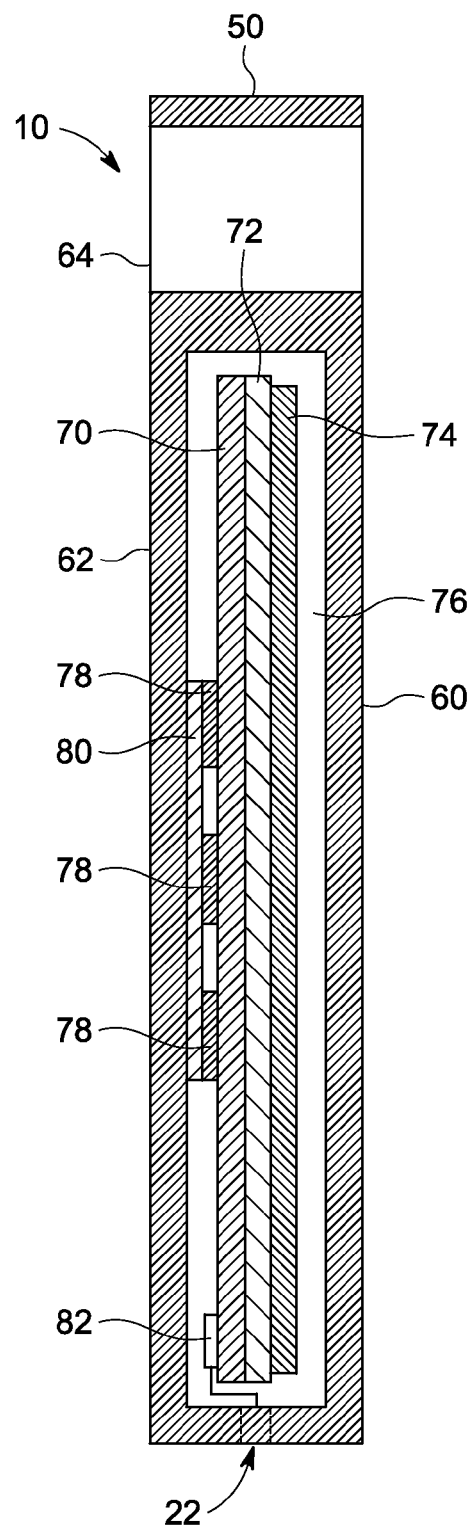
FIG. 3 is a side cut-away view of the portable detector shown in FIG. 2 viewed along the line 3-3 of FIG. 2.

FIG. 3 is a side cut-away view of the portable detector 10 shown in FIG. 2 viewed along the line 3-3 of FIG. 2. As shown in FIG. 3, the detector 10 also includes a circuit board 70 that is affixed to a panel support 72 that may be fabricated from a low N material, which in turn is affixed (e.g., using an adhesive) to a panel 74. The panel 74 may be a glass panel and may include X-ray scintillator material. In the exemplary embodiment, the panel 74 includes a scintillator. As such, during operation, the panel 74 is formed to include a plurality of detector rows that each includes a plurality of detector elements (not shown), that together sense the projected X-rays that pass through an object, such as a patient. During operation, each detector element produces an electrical signal that represents the intensity of an impinging X-ray beam and hence allows estimation of the attenuation of the beam as the beam passes through the subject 18. In some embodiments, the panel support 72 is not used, and circuit board 70 is affixed directly to the panel 74. Together, circuit board 70 and panel 74 (and panel support 72, if present) comprise an "electronic assembly."

To provide some degree of break resistance for panel 74, a gap 76 is provided between the panel 74 and the front cover 60. Also, the electronic assembly does not physically contact any wall of the casing 50, but is mounted to the back cover 62. Additionally, heat generating components 78 on the circuit board 70 may be thermally coupled to back cover 62 using a heat conducting compound 80. The heat conducting compound 80 provides, directly or indirectly, a mechanical coupling between the circuit board 70 and the back cover 62. In the exemplary embodiment, the portable detector 10 also includes a processor 82 that is mounted to the circuit board 70. The processor 82 is configured to store information to operate the portable detector 10 and/or to transmit information to a remote location via the wireless transceiver as discussed above. In the exemplary embodiment, the docking connector 22 and the processor 82 form a portion of an exemplary connector monitoring circuit 120 (shown in FIG. 6) which is discussed in more detail below. Specifically, the processor 82 is programmed to receive inputs, and based on the received inputs, determine when at least one of the docking connector 22 or the connector 16 should be cleaned or replaced.

In the exemplary embodiment, the detector 10 is portable, but typically large enough to image a significant region of a human patient, such as a patient's chest. Thus, the portable detector 10 may be only about one or a few centimeters in thickness, but may be tens of centimeters in width and length. In one embodiment, the portable detector 10 also includes an X-ray grid or anti-scatter grid, or some other grid appropriate for medical X-ray imaging. Referring again to FIG. 3, the portable detector also includes the docking connector 22. The docking connector 22 enables a remote station such as, the medical imaging system 12, to provide power to and communicate with the portable detector 10. Optionally, the portable detector 10 may be operated using a battery (not shown) and communicate with the remote station 12 via the wireless links discussed above.

Figure 4:
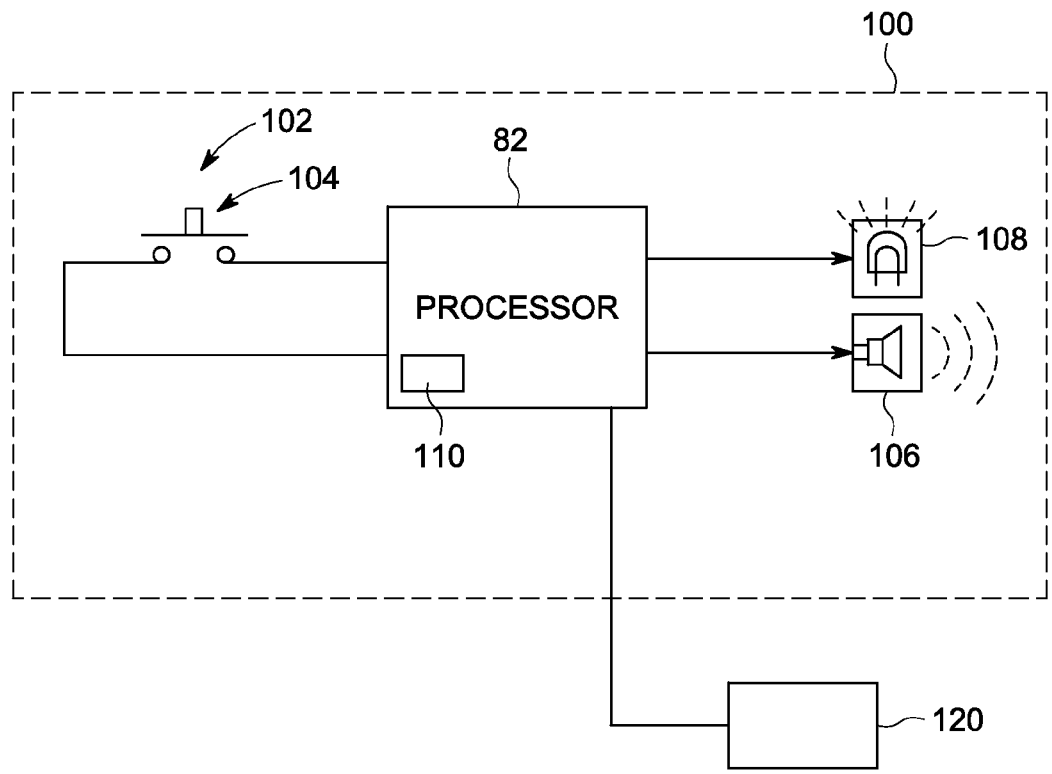
FIG. 4 is a schematic illustration of an exemplary power control circuit that may be used with the detector shown in FIGS. 1-3 in accordance with an embodiment of the present invention.

FIG. 4 is a schematic illustration of an exemplary power control circuit 100 that may be used with the portable detector shown in FIGS. 1-3 in accordance with an embodiment of the present invention. The power control circuit 100 includes a multi-function switch 102 that is coupled to a processor such as the processor 82. In the exemplary embodiment, the multi-function switch 102 is embodied as a pushbutton switch that is actuated by depressing and releasing a button 104 on the switch 102. The multi-function switch may include a spring mechanism (not shown) that biases the switch 102 in an "out", "unpressed" or "deactivated" position such that a current flow through the switch is terminated. When the button 104 is depressed the switch enables current to flow therethrough. Optionally, the multi-function switch 102 may be embodied as a spring-loaded selector switch, a toggle switch, a joystick, or other types of switches such as a touchscreen switch. The power control circuit 100 also includes an audible indicator 106 and a visual indicator 108. The audible indicator may be embodied, for example, as a speaker. The visual indicator 108 may be embodied, for example, as a light emitting diode (LED). During operation, the processor 82 transmits signals to each of the audible indicator 106 and the visual indicator 108 to activate each device.

The power control circuit 100 further includes a detector control module 110. The detector control module 110 may be implemented as a software program that is installed on the processor 82. Optionally, the detector control module 110 may be implemented as a hardware device such as an application specific integrated circuit (ASICs), a logic circuit, or any other circuit or processor capable of executing the functions described herein. During operation, the detector control module 110 is configured to utilize a signal received from the multi-function switch to reconfigure the detector 10 in different modes of operation to reduce power consumption and perform other functions as described in further detail below. During operation, the power control circuit 100 enables the portable detector 10 to operate in a plurality of operational modes. For example, in the detector sleep mode power is conserved by deactivating components within the portable detector 10 that consume the majority of power while the remaining components, e.g. the multi-function switch and the processor 82 remain activated to enable the operator to operate the multi-function switch and thus to configure the detector in other modes as discussed below. In a "wake up" mode of operation, the portable detector 10 is configured to transition from the "sleep mode" to an "active" or "idle" mode. In the idle mode, the multi-function switch 102 is operated such that power is supplied to the multi-function switch 102, the processor 82, the transceiver 544, and the detector electronics, e.g. the panel 74. In the idle mode, the detector 10 is configured to communicate with a remote station, such as the medical station 12. In some operational modes, only a portion of the detector elements on the panel 74 may be activated to perform imaging.

It should be realized that portable detector 10 is configured to operate in a plurality of operational modes. Moreover, the power consumed by the portable detector may be different in each operational mode. For example, in the sleep mode, the portable detector consumes relatively little power. Whereas, in the active mode, the portable detector consumes more power than when the portable detector is operated in the sleep mode. Additionally, even if the portable detector is operated in the active mode, some of the detector elements may not be utilized for imaging, therefore, the portable detector may consume more power than in the sleep mode, but less power than when operating in the fully active mode.

Therefore, the portable imaging system detector 10 is configured to operate in a plurality of operational modes, wherein at least some of the operational modes consume a quantity of power that is different than the power consumed in other operational modes. Moreover, the processor 82 is configured to, or programmed to, determine the operational mode that the portable detector is operating in. Once, the operational mode of the portable detector 10 is determined, the power consumed by the portable detector 10 in this mode is determined. In one embodiment, the power consumed by the portable detector 10 may be determined by physical measurement. Optionally, the power consumed by the portable detector 10 in each operational mode may be determined based on a priori knowledge. For example, during initial setup, various power measurements may be made on the portable detector 10 while the portable detector is operated in each operational mode. The measurements may then be stored in a look-up table for example, on the processor 82. During normal operation, the look-up table may then be accessed, by the processor 82, to determine the power consumed by the portable detector 10 based on the operational mode of the portable detector 10.

Figure 5:
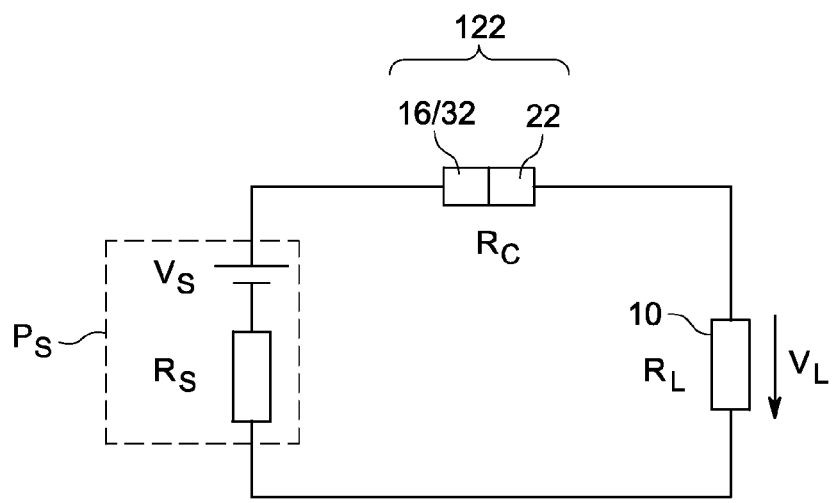
FIG. 5 is a simplified schematic illustration of an exemplary electrical circuit for coupling the portable detector to a power supply in accordance with an embodiment of the present invention.

To explain the general electrical operation of the portable detector 10, reference is now made to FIG. 5. FIG. 5 is a simplified schematic illustration of the electrical circuit coupling the portable detector 10 to an exemplary power supply, such as the medical imaging station 12 or the docking station 30. In the exemplary embodiment, $P_S$ represents the power supplied to the portable detector from an exemplary power source such as is supplied to the portable detector 10 from a power source such as the medical imaging station 12 or the docking station 30. In the exemplary embodiment, the power source $P_S$ is a direct current (DC) power source having a voltage output $V_S$ and an internal resistance $R_S$. Therefore, during normal operation, the exemplary power source $P_S$ outputs a relatively constant voltage referred to herein as a power source baseline voltage. It should be realized that each power source may have a different baseline voltage. Accordingly, the baseline voltage of each exemplary power source that may be utilized to supply power to the portable detector 10 may determined and the values representing the baseline voltage $V_S$ and the internal resistance $R_S$ of the power source $P_S$ may be input to and stored within the memory of processor 82.

$R_L$ represents the voltage seen by the load during operation. In the exemplary embodiment, the load is the portable detector 10. During normal operation, the portable detector 10 receives a relatively constant voltage supply from the exemplary power source $P_S$. Moreover, the portable detector consumes a relatively constant quantity of power during operation. Accordingly, the baseline power consumed by the portable detector, and thus the baseline voltage required to be received by the portable detector 10 to facilitate normal operation may be determined and the values may be input to and stored within the memory of processor 82.

It should be realized that during normal operation, the portable detector 10 is configured to operate in a plurality of operational modes as discussed above. Moreover, it should be realized that in each operational mode the portable detector 10 consumes a different amount of power. For example, in the sleep mode, the portable detector 10 consumes less power than when operated in the active mode. Accordingly, the operational mode of the portable detector 10 may be determined by the power control circuit 100 and then stored in the memory of the processor 82. Thus, in the exemplary embodiment, the power and voltage delivered to, and/or consumed by, the portable detector 10 is determined for each mode of operation and then stored in the memory of the processor 82. Thus, $V_L$ represents the voltage supplied to, and ($I_L \times V_L$) the power consumed by, the detector electronics 74 in each operational mode.

$R_C$ represents the resistance of the mating connector pair coupling the portable detector 10 to the power supply. For example, a mating pair 122 may include the connectors 22 and 16 or the mating pair 122 may include the connectors 22 and 32. During operation, at least one of the mating pair of connectors, for example connector 22 or 16 wears due to the mating cycles. The wear causes the resistance measured across the mating pair to change. In the exemplary embodiment, the resistance across the mating pair decreases as the number of mating cycles increases. Accordingly, the wear of the mating pairs may be calculated based on the voltage generated by the power supply $P_s$ and the voltage $V_L$ seen at the portable detector 10.

More specifically, as discussed above, for the exemplary portable detector 10, during operation $V_S$ and $R_S$ are approximately constant and can be determined for each power supply used to provide power to the portable detector 10. Additionally, for each operational mode, $R_L$ and $V_L$ may also be determined. Therefore, the only variable that significantly affects the voltage supplied to the portable detector 10 is the mechanical condition of the electrical connector $R_C$, e.g. connector 22. Rc, in the exemplary embodiment, is determined by measuring the voltage across $R_L$. More specifically, the mechanical condition or wear of the electrical connector 22, based on a change in the resistance, may be determined by measuring the voltage across the detector electronics 74.

Figure 6:
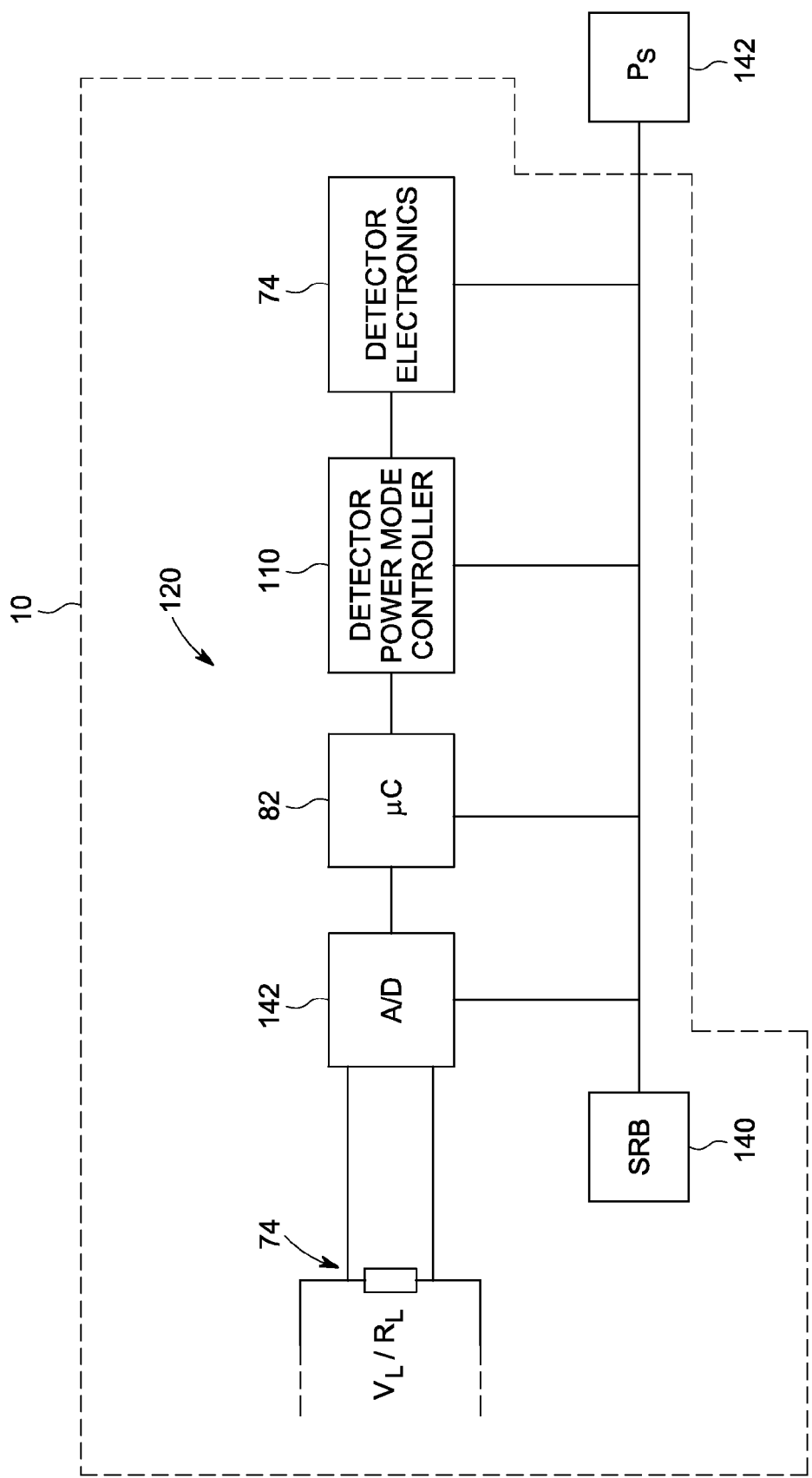
FIG. 6 is a simplified schematic illustration of the exemplary connector monitoring circuit that may be used with the detector shown in FIGS. 1-3 in accordance with an embodiment of the present invention.

FIG. 6 is a simplified schematic illustration of the exemplary connector monitoring circuit 120 that is configured to determine the electrical conductivity or resistance of the mating pair 122. Based on the electrical conductivity of the mating pair 122, the connector monitoring circuit 120 is configured to determine the wear, or a change in the wear condition, of the docking connector 22 and also determine whether the docking connector 22 should be cleaned or replaced. In the exemplary embodiment, the connector monitoring circuit 120 includes a switching regulator board (SRB) 140 that is configured to regulate the internal voltages of the portable detector 10. The connector monitoring circuit 120 also included in the processor 82 and an analog-to-digital converter 142. During operation, the analog-to-digital converter 142 is coupled to, and receives an analog signal from, the portable detector that is representative of the voltage $V_L$ across the detector electronics 74. The analog-to-digital converter 142 converts the analog signal to a digital signal that is transmitted to the processor 82. The processor 82 then measures or determines the value of the voltage $V_L$.

For example, during operation, the input voltage of the detector $V_L$ is measured using the microcontroller 82 in accordance with:

$$V_L = \frac{R_L}{R_S + R_C + R_L} V_S.$$

Optionally, the input voltage may be measured directly from the A/D converter 142. In general, the power supply internal resistance $R_S$ is much less than the resistance seen at the portable detector $R_L$, and the resistance of the mating pair of connectors $R_C$ is approximately 0 when the mating pair of connectors are relatively new or have little or no wear. Thus, the input voltage of the detector $V_L$ is approximately equal to the power source voltage $V_S$. However, as the mating pair of connectors 122 experience wear or when there is physical contamination within the mating pair of connectors 122, the resistance of the mating pair of connectors $R_C$ increases and the corresponding input voltage $V_L$ to the portable detector 10 decreases. When the input voltage $V_L$ to the portable detector 10 decreases below a predetermined threshold, the processor 82 generates a visual or audio indication that the docking connector 22 or the connector 16 should be cleaned or replaced. It should be realized that that the operator should ascertain that the supply voltage has not decreased, because a decrease in the voltage supply may also cause a decrease in $V_L$, even if the connection is still "good". Furthermore, if $V_S$ increases, and the connection degrades, $V_L$ may "look" like it is still "good" and may not be.

Figure 7:
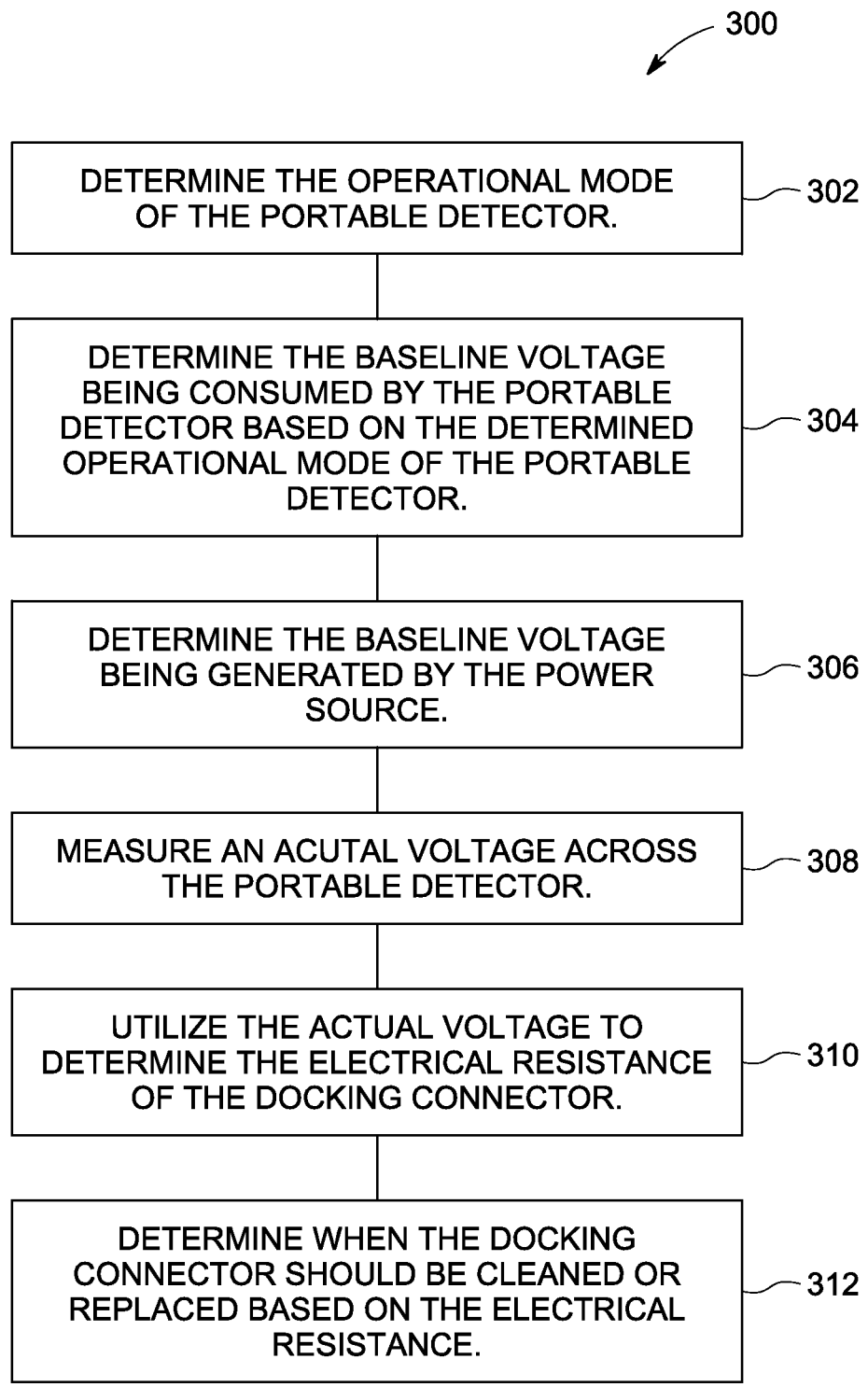
FIG. 7 is a flowchart of an exemplary method of operating the power control circuit shown in FIG. 6 in accordance with an embodiment of the present invention.

FIG. 7 is a flowchart of an exemplary method 300 of monitoring the wear of the docking connector 22 using the connector monitoring circuit 120 shown in FIG. 6. At 302, the connector monitoring circuit 120 determines the operational mode of the portable detector 10. For example, the processor 82 determines whether the portable detector 10 is operating in the sleep mode or the active mode based on an input received from the detector control module 110.

At 304, the connector monitoring circuit 120 determines the minimum baseline voltage $V_L$ that should be detected, e.g. by the A-to-D converter 142, by the portable detector 10 based on the operational mode determined at 302. For example, in the sleep mode, the baseline voltage detected by the portable detector 10 is more than the baseline voltage detected by the portable detector in the active mode. Typically, the current drawn by the detector in the sleep mode is less than current drawn by the detector in the active mode. Therefore, the drop across $R_S$ and $R_C$ is typically less in the sleep mode than in the active mode. Consequently, more of $V_S$ will appear across $R_L$. A value representing the baseline voltage $V_L$ for the determined operational mode is then stored in the memory of the processor 82.

At 306, the connector monitoring circuit 120 determines the baseline voltage $V_S$ being generated by the power supply. As discussed above, the power supply may be, for example, the medical station 12 or the docking station 30. In the exemplary embodiment, the baseline voltage $V_S$ being supplied by the power supply is determined based on previous measurements. A value representing the baseline voltage $V_S$ is then stored in the memory of the processor 82.

At 308, the connector monitoring circuit 120 measures the actual voltage being delivered to the portable detector 10. As discussed above, a disturbance, such as wear or contamination, of the electrical connection between the docking connector 22 and the connector 16 may result in a decrease of the electrical conductivity through the mating pair. The decrease in electrical conductivity is generally proportional to an increase in the resistivity of the mating pair. Therefore, as the resistance of the mating pair increases, the voltage supplied to the portable detector decreases proportionally. Therefore, at 308 the actual voltage being delivered to the portable detector 10 is measured.

At 310, the actual voltage measured at 308 is utilized to determine an electrical resistance of at least one of the docking connector 22 or the connector 16 in accordance with:

$$V_L = \frac{R_L}{R_S + R_C + R_L} V_S. \qquad \text{Equation 1}$$

where:
$V_L$ is the measured voltage at the portable detector;
$V_S$ is the voltage of the power source;
$R_L$ is the resistance of the portable detector based on the operational mode;
$R_S$ is the internal resistance of the power supply; and
$R_C$ is the resistance of the mating pair of connectors.

As discussed above, the values $V_S$, $R_S$, can be acquired by accessing the previously determined values stored in the processor 82. Moreover, the resistance $R_C$ of the mating pair of connectors can be calculated by measuring the voltage $V_L$ across the portable detector 10 and utilizing Equation 1 to calculate $R_C$.

In another embodiment, if the current (I), $V_S$ at the connector, and $V_L$ on the other side of the connector are all measured, because the components are all in series, all resistances will see the same current, thus $R_C$ may be computed directly as $(V_S-V_L)/I$. In this embodiment, knowledge of the operational mode and the mating cycles is not utilized because the current is measured directly. Measuring the current directly operates by maintaining a "constant", albeit arbitrary, operating mode while all three measurements are being made. This embodiment is advantageous in that during development, or during any part of the detector lifecycle, if the operating modes change in nature, recharacterization of the operating modes would be required unless current is measured directly. Effectively, to characterize the detector power consumption by operating mode is to characterize the current drawn by the detector as a function of operating mode. This information must then be "memorized" by the system for use in determining the need to clean or replace the connector. Measuring the current directly obviates the need for both characterization and memorization.

At 312, the connector monitoring circuit 120 determines when the docking connector 22 or the connector 16 should be cleaned or replaced based on the measured resistivity $R_C$ of the mating pair, and as discussed in more detail below.

Figure 8:
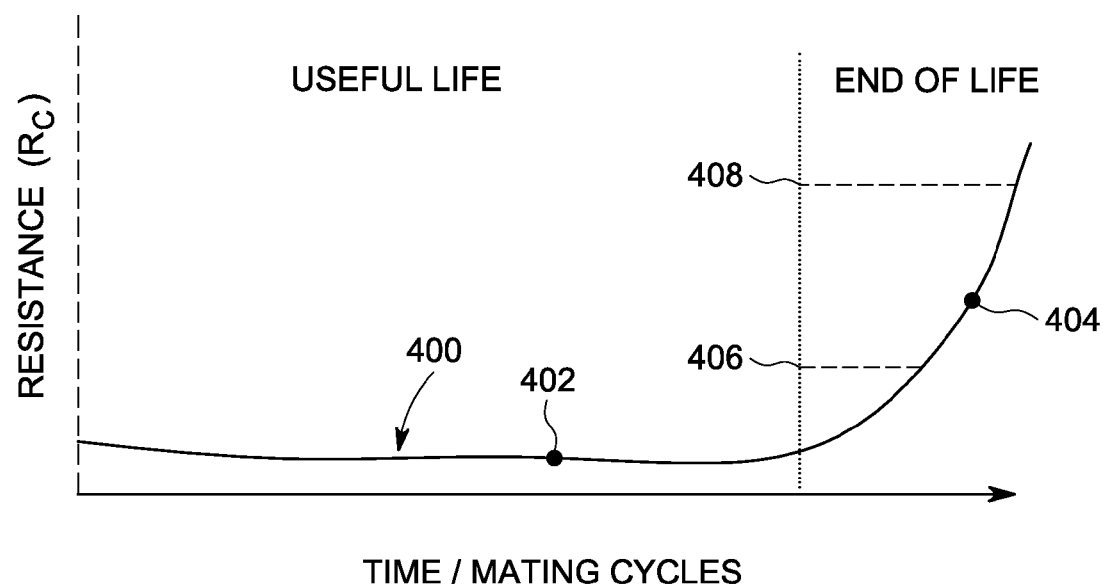
FIG. 8 is a graphical illustration of an exemplary connector wear curve in accordance with an embodiment of the present invention.

FIG. 8 is a graphical illustration of an exemplary wear curve 400 that may be utilized to determine when at least one of the docking connector 22 or the connector 16 should be cleaned or replaced based on the electrical resistivity $R_C$. In one exemplary embodiment, the wear curve 400 is derived by measuring the resistance of a plurality of conventional connectors connected, being the same type as the docking connector 22, together over a plurality of mating cycles. The X-axis represents time or mating cycles of the docking connector 22 and the connector 16. The Y-axis represents the resistivity $R_C$ of the mating pair. As shown in FIG. 7, when the mating cycles or usage time is relatively low, the electrical $R_C$ of the mating pair is relatively low. Thus the voltage $V_L$ measured at the portable detector 10 is approximately equal to the voltage $V_S$ being supplied by the power source. Because VL=VS*RL/(RS+RC+RL), the voltage is always proportional. When RL>>RS and RC, then the voltage is approximately equal. Thus, as RC increases due to wear, VL will shrink relative to VS. However, as the mating cycles increase over time, the electrical resistivity $R_C$ of the mating pair also increases resulting in a reduction of the voltage $V_L$ measured at the portable detector 10. In the exemplary embodiment, the values corresponding to the wear curve 400 are stored as a look-up table in the processor 82

In operation, once the electrical resistivity $R_C$ of the mating pair has been determined as described above, the value for the electrical resistivity $R_C$ is compared to the values stored in the look-up table generated using the wear curve 400. For example, a point 402 represents a first value for the electrical resistivity $R_C$ as calculated above. Moreover, a point 404 represents a second value for the electrical resistivity $R_C$ as calculated above. In one embodiment, when an electrical resistivity $R_C$ of the mating pair is less than a predetermined threshold 406, the connector monitoring circuit 120 is configured to prompt a user to clean the docking connector 22 or the connector 16, as discussed in more detail below. In the exemplary embodiment, the connector monitoring circuit 120 may activate a visual or audible alarm. For example, the visual alarm may be embodied as a color light or message that prompts the user to clean the docking connector 22. Optionally, the audio indicator may emit an audio indication or message to prompt the user to clean the docking connector 22.

However, when the electrical resistivity $R_C$ is greater than the threshold 406, e.g. point 404, and/or less than the threshold 408, the connector monitoring circuit 120 is configured to prompt a user to replace at least one of the docking connector 22 or the connector 16. In the exemplary embodiment, the connector monitoring circuit 120 may activate a visual or audible alarm. For example, the visual alarm may be embodied as a colored light or message that prompts the user to replace the docking connector 22. Optionally, the audio indicator may emit an audio indication or message to prompt the user to replace the docking connector 22. It should be realized that in the exemplary embodiment, the determination whether the docking connector 22 should be cleaned or replaced is based on the electrical resistivity $R_C$ of the docking connector. More specifically, when a difference between the voltage generated by the power supply and the voltage utilized by the load exceeds a predetermined threshold, the docking connector 22 is either cleaned or replaced. In the exemplary embodiment, the indication generated when the docking connector 22 requires cleaning is different than the indication generated when the docking connector requires replacement. The thresholds may be changed as desired or needed.

Optionally, when a given threshold is passed, the system may prompt the user to clean the connector, inhibiting use until the user indicates, through the system user interface, that cleaning was completed. At that point, the connection can be tested again. If the resistance exceeds a predetermined threshold, then the system can generate a message that instructs the operator to replace the connector.

Figure 9:
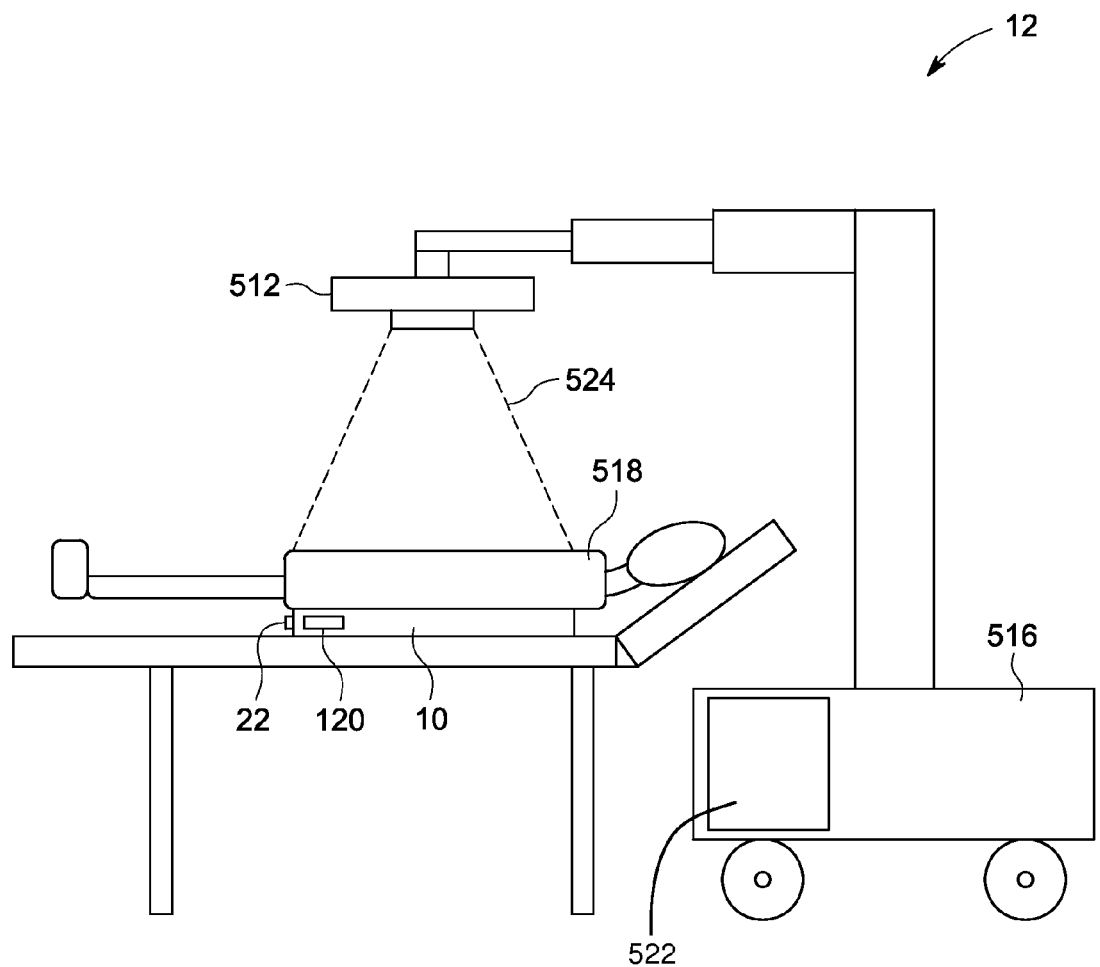
FIG. 9 is a pictorial view of the exemplary medical imaging system shown in FIG. 1 in accordance with an embodiment of the present invention.
Figure 10:
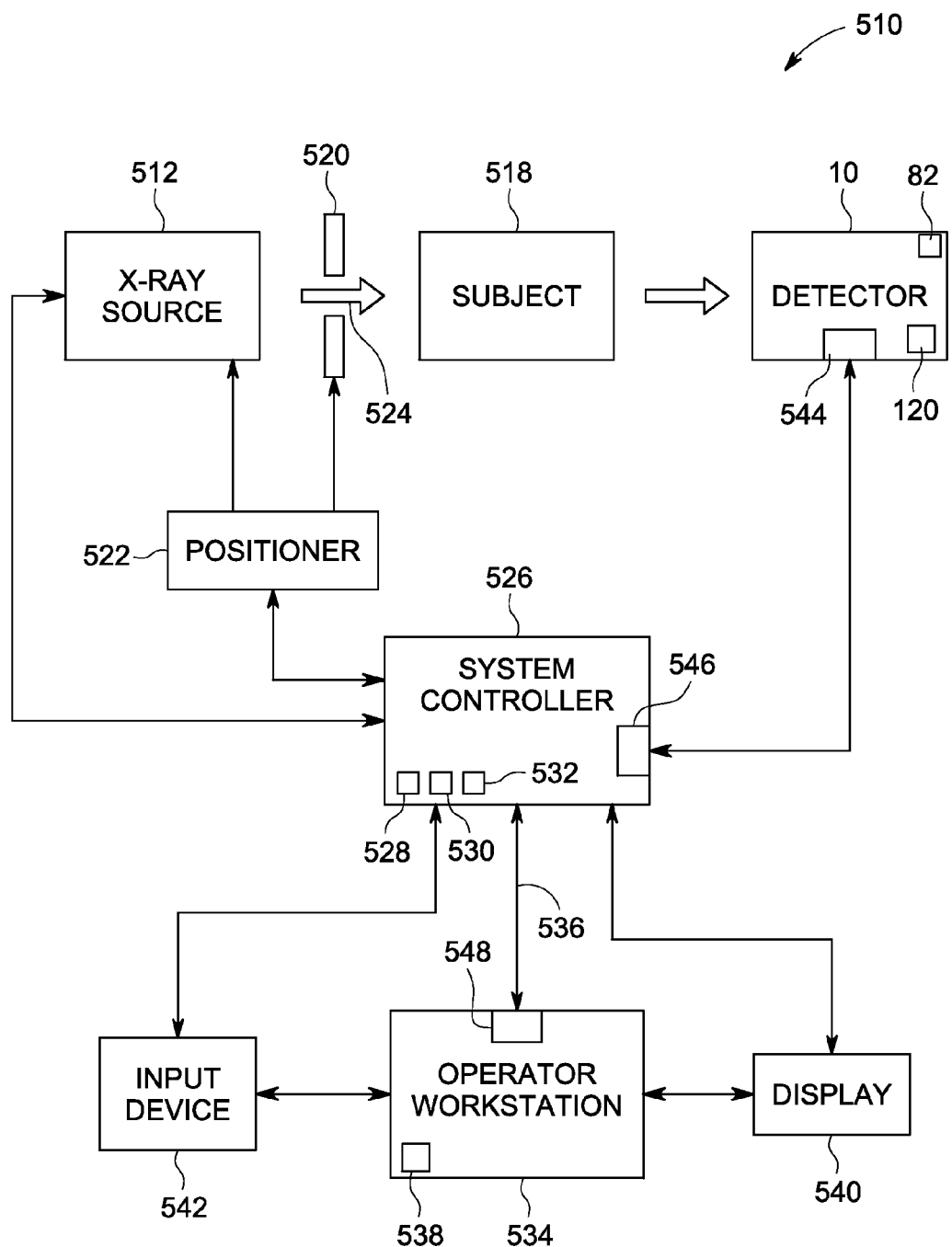
FIG. 10 is a block schematic diagram of the exemplary medical imaging system shown in FIG. 9 in accordance with an embodiment of the present invention.

FIG. 9 is a pictorial view of the exemplary medical imaging system 12 which may be utilized to control the operations of the portable detector 10 described above. FIG. 10 is a block schematic diagram of the exemplary medical imaging system 12 shown in FIG. 9 in accordance with an embodiment of the present invention. The medical imaging system 12 in the exemplary embodiment is a digital radiography imaging system that includes an X-ray source 512 and the portable detector 10. As shown in FIG. 9, the X-ray source 512 is mounted to a gantry 516. The gantry 516 is movable to enable the X-ray source 512 to be properly positioned with respect to a subject 518 being imaged or to enable the X-ray source 512 to be moved from one imaging room to another. Optionally, the gantry 516 is stationarily mounted by coupling the gantry to a floor, for example. Referring to FIG. 9, the imaging system 12 may also include a collimator 520 that is disposed between the X-ray source 512 and the subject 518. The imaging system 12 may also include a positioner 522. The positioner 522 is a mechanical controller coupled to the X-ray source 512 and collimator 520 for controlling the positioning of the X-ray source 512 and the collimator 520.

During operation, the imaging system 12 generates images of the subject 518 by means of an X-ray beam 524 emitted by the X-ray source 512, and passing through the collimator 520. The collimator 520 forms and confines the X-ray beam 524 to a desired region, wherein the subject 518, such as a human patient, an animal or an object, is positioned. A portion of the X-ray beam 524 passes through or around the subject 518 and, being altered by attenuation and/or absorption by tissues within the subject 518, continues on toward and impacts or impinges on the portable detector 10. In one embodiment, the portable detector 10 may be mounted within the system as if it were a fixed detector in a fixed position. In the exemplary embodiment, the detector 10 is a portable digital flat panel X-ray detector. During operation, the detector 10 converts X-ray photons to lower energy light photons, and subsequently to electric signals, which are acquired and processed to reconstruct an image of internal anatomy of the subject 518.

Referring again to FIG. 10, the imaging system 12 further includes a system controller 526 coupled to the X-ray source 512, the detector 10, and the positioner 522 for controlling operation of the X-ray source 512, the detector 10, and the positioner 522. The system controller 526 may supply both power and control signals for imaging examination sequences. In general, the system controller 526 controls the operation of the imaging system 12 to execute examination protocols and to process acquired image data. The system controller 526 may also include signal processing circuitry, based on a general purpose or application-specific computer, associated memory circuitry for storing programs and routines executed by the computer, as well as configuration parameters and image data, interface circuits, and so forth.

The system controller 526 may further include at least one computer or processor 528 that is configured to coordinate the operation of the X-ray source 512, the detector 10, and the positioner 522, and to process image data acquired from the detector 10. As used herein, the term "computer" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 528 carries out tasks in accordance with routines stored in an associated memory circuitry 530. The associated memory circuitry 530 may also serve to store configuration parameters, imaging protocols, operational logs, raw and/or processed image data, and so forth.

The system controller 526 may further include interface circuitry 532 that permits an operator or user to define imaging protocols, imaging sequences, determine the operational status and health of system components, and so-forth. The interface circuitry 532 may allow external devices to receive images and image data, and command operation of the radiography system, configure parameters of the system, and so forth.

The system controller 526 may be coupled to a range of external devices via a communications interface. Such devices may include, for example, an operator workstation 534 for interacting with the system controller 526 or directly to the imaging system, processing or reprocessing images, viewing images, and so forth. The operator workstation 534 may be embodied as a personal computer (PC) that is positioned near the imaging system 12 and hard-wired to the system controller 526 via a communication link 536. The workstation 534 may also be embodied as a portable computer such as a laptop computer or a hand-held computer that transmits information to the system controller 526. In one embodiment, the communication link 536 may be hardwired between the system controller 526 and the workstation 534. Optionally, the communication link 536 may be a wireless communication link that enables information to be transmitted to or from the workstation to the system controller 526 wirelessly. In the exemplary embodiment, the workstation 534 controls real-time operation of the imaging system 12. The workstation 534 is also programmed to perform medical image diagnostic acquisition and reconstruction processes described herein.

Accordingly, the operator workstation 534 includes a central processing unit (CPU) or computer 538, a display 540 and an input device 542. In the exemplary embodiment, the computer 538 executes a set of instructions that are stored in one or more storage elements or memories, in order to process input data. The storage elements may also store data or other information as desired or needed. The storage element may be in the form of an information source or a physical memory element within the computer 538. The set of instructions may include various commands that instruct the computer or processor 538 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 538 connects to the communication link 536 and receives inputs, e.g., user commands, from the input device 542. The input device 542 may be, for example, a keyboard, mouse, a touch-screen panel, and/or a voice recognition system, etc. Through input device 542 and associated control panel switches, the operator can control the operation of the imaging system 12 and the positioning of the X-ray source 512 for a scan. Similarly, the operator can control the display of the resulting image on the display 540 and can perform image-enhancement functions using programs executed by the workstation CPU 538. The workstation 534 may also be linked to the system controller 526 by any one or more network links.

In the exemplary embodiment, to transmit the electric signals from the detector 10 to the system controller 526 or the workstation 534, the detector 10 includes a transceiver 544 that is configured to transmit the electrical signals and other information generated by the detector 10 in a wireless format to a corresponding transceiver 546 that is mounted in the system controller 526. Optionally, the transceiver 544 is configured to transmit the electrical signals and other information generated by the detector 10 in a wireless format to a corresponding transceiver 548 that is mounted in the workstation 534.

Described herein is a portable detector 10 that includes a connector monitoring circuit that is configured to determine the electrical conductivity or resistance of the mating pair. Based on the electrical conductivity of the mating pair, the connector monitoring circuit is configured to determine the wear on the docking connector and also determine whether the docking connector should be cleaned or replaced. Optionally, the connector monitoring circuit may also determine the connector wear by counting the mating cycles. More specifically, because the detector is portable, the detector may be utilized with various different imaging systems. Thus, the quantity of mating cycles may be counted by the detector itself or by the system to which the portable detector is connected.

A technical effect of the various embodiments is to notify an operator that the electrical connector on the portable detector requires cleaning or replacement. A visual or audible indication enables the operator to clean or replace the electrical connector is provided.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose various embodiments of the invention, including the best mode, and also to enable any person skilled in the art to practice the various embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of monitoring the voltage transmitted through a pair of electrical connector devices, the pair of electrical connector devices including a source connector coupled to a power supply and a load connector coupled to a load, the source connector being coupled to the load connector, said method comprising:
   determining the voltage detected at the load;
   determining the voltage generated by the power supply; and
   determining an electrical resistance of the pair of electrical connectors using the determined voltage detected at the load and the voltage generated by the power supply.

2. A method in accordance with claim 1 further comprising:
   comparing the determined electrical resistance to a predetermined threshold; and
   determining the wear of at least one of the load connector or the source connector based on the comparison.

3. A method in accordance with claim 1 wherein determining the voltage detected at the load further comprises determining the voltage detected at a portable imaging system detector.

4. A method in accordance with claim 3 wherein the portable imaging system detector is configured to operate in a plurality of operational modes, said method further comprising determining an electrical resistance of the pair of electrical connectors based on the operational mode of the portable imaging system detector.

5. A method in accordance with claim 1 further comprising prompting a user to replace at least one of the source connector or the load connector based on the determined electrical resistance.

6. A method in accordance with claim 1 further comprising prompting a user to clean at least one of the source connector or the load connector based on the determined electrical resistance.

7. A method in accordance with claim 1 further comprising prompting a user to clean at least one of the source connector or the load connector when the electrical resistance is greater than a first predetermined threshold and less than a second predetermined threshold.

8. A method in accordance with claim 1 further comprising a user to replace at least one of the source connector or the load connector when the electrical resistance is greater than a predetermined threshold.

9. A method in accordance with claim 1 further comprising generating at least one of a visual or audible signal when a difference between the voltage generated by the power supply and the voltage utilized by the load exceeds a predetemrined threshold.

10. A method in accordance with claim 1 further comprising:
   generating a first indication when at least one of the source connector or the load connector requires cleaning; and
   generating a different second indication when at least one of the source connector or the load connector requires replacement.

11. A connector monitoring assembly comprising:
an analog-to-digital converter; and
a processor coupled to the analog-to-digital converter, the processor programmed to
determine a voltage detected at a portable imaging system detector;
determine a voltage generated by a power supply; and
determine an electrical resistance of a pair of electrical connectors using the determined voltage detected at the portable imaging system detector and the voltage generated by the power supply, the pair of electrical connector devices including a source connector coupled to the power supply and a load connector coupled to the portable imaging system detector, the source connector being coupled to the load connector.

12. A connector monitoring assembly in accordance with claim 11 wherein the processor is further programmed to:
   compare the determined electrical resistance to a predetermined threshold; and
   determine the wear of at least one of the load connector or the source connector based on the comparison.

13. A connector monitoring assembly in accordance with claim 11 wherein the portable imaging system detector is configured to operate in a plurality of operational modes, the processor is further programmed to determine an electrical resistance of the pair of electrical connectors based on the operational mode of the portable imaging system detector.

14. A connector monitoring assembly in accordance with claim 11 wherein the processor is further programmed to prompt a user to clean or replace at least one of the source connector or the load connector based on the determined electrical resistance.

15. A connector monitoring assembly in accordance with claim 11 wherein the processor is further programmed to prompt a user to clean at least one of the source connector or the load connector when the electrical resistance is greater than a first predetermined threshold and less than a second predetermined threshold.

16. A connector monitoring assembly in accordance with claim 11 wherein the processor is further programmed to:
   determine, based on the electrical resistance, if at least one of the source connector or the load connector requires cleaning or replacement;
   generate, via at least one of an audible or visual indicator, a first indication when the at least one of the source connector or the load connector requires cleaning; and
   generate, via the at least one of the audible or visual indicator, a different second indication when the at least one of the source connector or the load connector requires replacement.

17. A portable X-ray detector comprising:
   a detector panel including a plurality of detector elements;
   a docking connector configured to provide electrical power to the detector panel, the docking connector configured to couple to a power connector; and
   a connector monitoring assembly coupled to the docking connector, the connector monitoring assembly configured to
   determine a voltage detected at a detector panel;
   determine a voltage generated by a power supply; and
   determine an electrical resistance of the docking connector using the determined voltage detected at the detector panel and the voltage generated by the power supply.

18. The portable X-ray detector of claim 17 wherein the connector monitoring circuit is further configured to:
   compare the determined electrical resistance to a predetermined threshold; and
   determine the wear of the docking connector based on the comparison.

19. The portable X-ray detector of claim 18 wherein the portable imaging system detector is configured to operate in a plurality of operational modes, the connector monitoring circuit is further configured to determine the electrical resistance of the docking connector based on the operational mode of the portable imaging system detector.

20. The portable X-ray detector of claim 18 wherein the connector monitoring circuit is further configured to prompt a user to clean or replace the docking connector based on the determined electrical resistance.

21. The connector monitoring assembly of claim 15 wherein the processor is further configured to generate an indication that instructs an operator to replace the at least one of the source connector or the load connector when the electrical resistance exceeds a predetermined threshold after the connector has been cleaned.

* * * * *